(12) United States Patent
Norris et al.

(10) Patent No.: US 9,402,755 B2
(45) Date of Patent: *Aug. 2, 2016

(54) SLEEVE RETRACTION SYSTEM

(71) Applicant: W. L. Gore & Associates, Inc., Newark, DE (US)

(72) Inventors: Patrick M. Norris, Flagstaff, AZ (US); Matthew G. Sondreaal, Phoenix, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/743,174

(22) Filed: Jan. 16, 2013

(65) Prior Publication Data

US 2013/0245743 A1    Sep. 19, 2013

Related U.S. Application Data

(60) Provisional application No. 61/610,389, filed on Mar. 13, 2012.

(51) Int. Cl.
| | | |
|---|---|---|
| *A61F 2/06* | (2013.01) | |
| *A61F 2/95* | (2013.01) | |
| *A61F 2/966* | (2013.01) | |
| *A61F 2/97* | (2013.01) | |

(52) U.S. Cl.
CPC . *A61F 2/95* (2013.01); *A61F 2/966* (2013.01); *A61F 2/97* (2013.01); *A61F 2002/9665* (2013.01)

(58) Field of Classification Search
CPC ... A61F 2/95; A61F 2002/9665; A61F 2/966; A61F 2/97
USPC ................................................ 623/1.23, 1.13
See application file for complete search history.

(56) References Cited

U.S. PATENT DOCUMENTS

| | | | | |
|---|---|---|---|---|
| 5,554,183 | A * | 9/1996 | Nazari ........................ | 623/1.49 |
| 2004/0122503 | A1* | 6/2004 | Campbell et al. ........... | 623/1.12 |
| 2005/0154443 | A1* | 7/2005 | Linder et al. ................. | 623/1.11 |
| 2007/0142896 | A1* | 6/2007 | Anderson et al. ............ | 623/1.13 |
| 2010/0145430 | A1* | 6/2010 | Wubbeling et al. .......... | 623/1.11 |
| 2012/0022630 | A1* | 1/2012 | Wubbeling .................. | 623/1.11 |

FOREIGN PATENT DOCUMENTS

| | | |
|---|---|---|
| WO | 00/13613 | 3/2000 |
| WO | 2009/126906 | 10/2009 |
| WO | 2010/063795 | 6/2010 |

OTHER PUBLICATIONS

International Search Report for PCT/US2013/022415 mailed May 3, 2013, corresponding to U.S. Appl. No. 13/743,174.

* cited by examiner

*Primary Examiner* — Richard Louis

(57) ABSTRACT

The present disclosure describes systems for endoluminal devices utilizing a sleeve for constraining an expandable device toward a constrained configuration suitable for endoluminal delivery to a treatment site along vasculature; and a mechanism for retracting at least a portion of the sleeve.

20 Claims, 2 Drawing Sheets

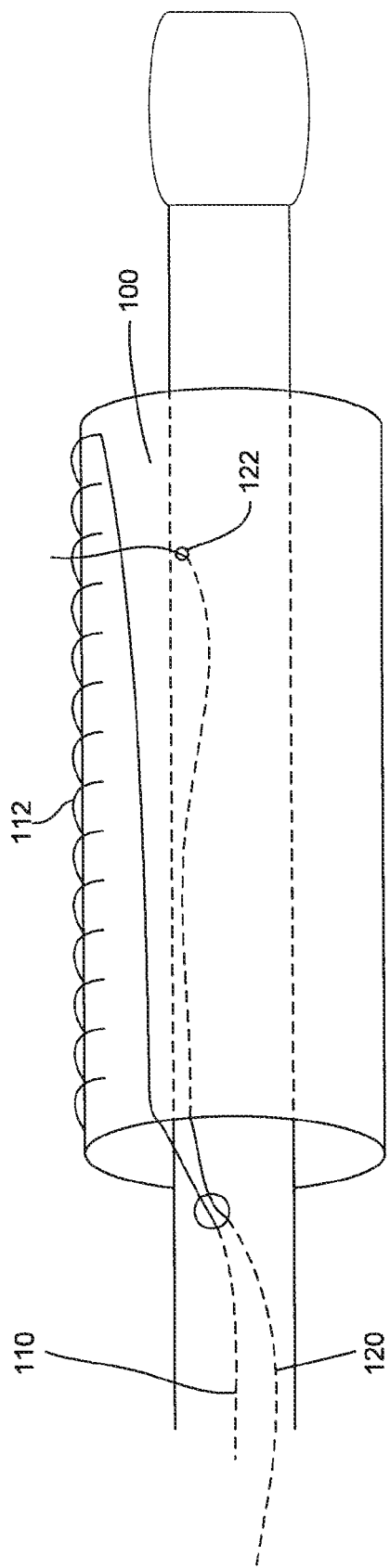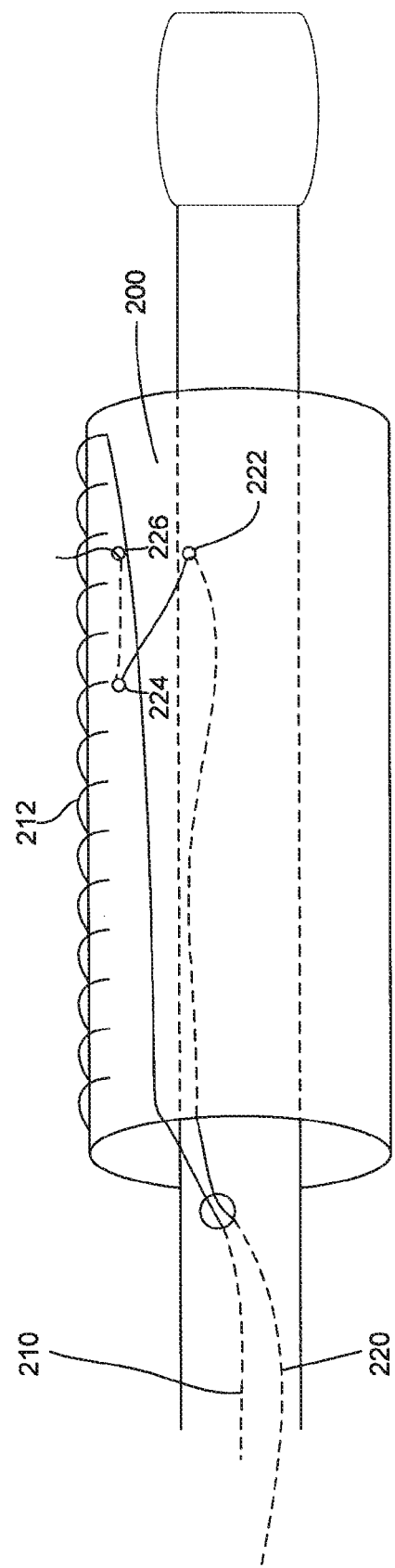

SLEEVE RETRACTION SYSTEM

CROSS-REFERENCE TO RELATED APPLICATIONS

This application claims priority to U.S. Provisional Application Ser. No. 61/610,389, entitled "SLEEVE RETRACTION SYSTEM" and filed Mar. 13, 2012, which is hereby incorporated by reference in its entirety.

BACKGROUND

1. Field

The present disclosure relates generally to endoluminal devices and, more specifically, to endoluminal devices having a sleeve.

2. Discussion

Endoluminal devices are frequently used to treat the vasculature of human patients. It is generally known to utilize a flexible sleeve for constraining the device toward a outer peripheral dimension or delivery configuration suitable for endoluminal delivery toward a vascular treatment site. It may be desirable to at least partially retract such a sleeve, for example, a sleeve configured to remain in situ after deployment of the underlying endoluminal device, for example, so as to prevent inadvertent obstruction of a branch vessel by the sleeve. Clinicians may not be able to rely exclusively on conventional imaging technologies to avoid such inadvertent obstruction because, inter alia, (i) such imaging technologies may not detect sleeves themselves, (ii) sleeves may not comprise radioopaque markers, and (iii) radioopaque bands or other markers on endoluminal devices may not necessarily correlate to the ends of sleeves. Thus, there is a need for systems that provide such sleeve retraction characteristics.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein:

FIG. 1 illustrates a sleeve retraction system;

FIG. 2 illustrates a sleeve retraction system having a z-pattern; and

DETAILED DESCRIPTION

Figure 3:
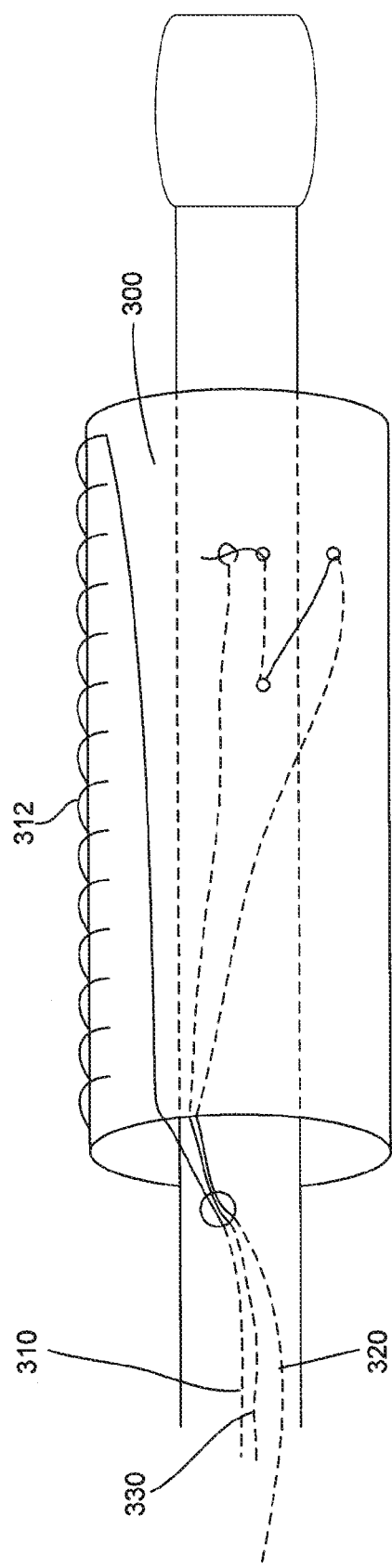
FIG. 3 illustrates a sleeve retraction system having a z-pattern, wherein a sleeve pull back line is engaged to a release line.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure can be described in connection with various principles and beliefs, the present disclosure should not be bound by theory.

Endoluminal devices are frequently used to treat the vasculature of human patients. These treatments or procedures are commonly referred to as intraluminal or endovascular procedures. Such devices often include a sleeve.

With reference to FIG. 1, systems of the present disclosure comprise a sleeve 100 for constraining an endoluminal device, one or more deployment lines 110, and one or more sleeve pull back lines 120.

As used herein, the term "sleeve" refers to a primary, secondary, tertiary, etc., sleeve, sheath, or the like, that constrains an endoluminal device toward a collapsed configuration or outer peripheral dimension suitable for endoluminal delivery of the device to a treatment portion of the vasculature of a patient.

For the purposes of the disclosure, the term "constrain" may mean (i) to limit the expansion, either through self-expansion or assisted by a device, of the diameter of an endoluminal device or (ii) to cover or surround but not otherwise restrain an endoluminal device (e.g., for storage or biocompatibility reasons and/or to provide protection to the endoluminal device and/or the vasculature).

Potential materials for the sleeve 100 include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for the sleeve 100 material can include high strength polymer fibers such as ultra high molecular weight polyethylene fibers (e.g., Spectra®, Dyneema Purity®, etc.) or aramid fibers (e.g., Technora®, etc.). The sleeve 100 may include a bioactive agent. Any sleeve which may be used to constrain an endoluminal device is in accordance with the present disclosure.

As used herein, the term "endoluminal device" or "device" refers to stents, grafts, filters, valves, anchors, occluders, and other implantable devices, and also includes all of the foregoing constrained in one or more sleeves.

As used herein, the term "line" refers to any type of string, cord, thread, fiber, or wire, can comprise metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol; and high strength polymer fibers such as ultra high molecular weight polyethylene fibers (e.g., Spectra®, Dyneema Purity®, etc.) or aramid fibers (e.g., Technora®, etc.).

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

In various embodiments, the deployment line 110 is suitably configured to form a coupling 112 which closes the sleeve 100 by coupling adjacent parallel edges of the sleeve 100. As used herein, the term "coupling" refers to any coupling, stitch (e.g., a chain stitch), thread, weave pattern, etc., which may be used to close the sleeve 100, and which may be released by applying tension to the deployment line 110.

In various embodiments, the sleeve pull back line 120 is engaged to the coupling 112. As used herein, the term "engaged" refers to a fixed or moveable coupling between at least two elements, enabled by now known or as yet unknown methods, for example, by compression, friction, knots, sutures, holes, loops, rings, clips, or the like. In an illustrative embodiment, the sleeve pull back line 120 is fixedly engaged to the coupling 112 toward the proximal end of the sleeve 100. The engagement between the sleeve pull back line 120 and the coupling 112 may occur on the exterior of, the interior of, and/or through the sleeve 100.

In various embodiments, the sleeve pull back line 120 is further engaged to the sleeve 100. In an illustrative embodiment, the sleeve pull back line 120 is moveably engaged to the proximal end of the sleeve 100, for example, threaded through a hole 122. Similar to above, the engagement between the sleeve pull back line 120 and the sleeve 100 may occur on the exterior of, the interior of, and/or through the sleeve 100.

In various embodiments, the sleeve 100 is retracted from a device by applying tension to the sleeve pull back line 120. The sleeve 100 may be fully or partially retracted and may be retracted equally along its axial length or equally and "scrunched" at its proximal or distal end.

In addition, the sleeve pull back line 220 may be threaded through a plurality of holes in the sleeve 200 to evenly distribute and/or multiply the tensile force applied to the sleeve pull back line 120 on the sleeve 200. For example, and with reference now to FIG. 2, the sleeve pull back line 220 may be threaded through holes 222, 224, 226 in the proximal end of the sleeve 200 in a z-pattern. The sleeve pull back line 220 is shown with a solid line being on the exterior of the sleeve 200 and a dashed line being on the interior of the sleeve 200. In this manner the tensile force applied to the sleeve pull back line 120 can be multiplied, for example, by a factor of approximately 2 or more.

In various embodiments, as tension is applied to the end of the deployment line 210 and the coupling 212 is released past a point of engagement with the sleeve pull back line 220, the sleeve pull back line 220 is disengaged from the coupling 212. Disengaging the sleeve pull back line 220 from the coupling 212 thereby breaks tension in the sleeve pull back line 220 and, consequently, sleeve retraction ceases. In addition, disengaging the sleeve pull back line 220 from the coupling 212 renders the sleeve pull back line 220 removeable by an operator.

The relative timing of when disengagement of the sleeve pull back line 220 from the coupling 212 occurs, and thus how much the sleeve 200 is retracted by the sleeve pull back line 220, can either be determined manually or be preconfigured.

In embodiments where the disengagement is determined manually, the deployment line 210 and the sleeve pull back line 220 can be pulled sequentially by an operator. For example, tension can be applied to the sleeve pull back line 220 until the desired amount of sleeve retraction has occurred, whereupon tension can be applied to the deployment line 210 to release the coupling 212 past a point of its engagement with the sleeve pull back line 220, causing the disengagement of the sleeve pull back line 220 from the coupling 212.

In embodiments where the disengagement of the sleeve pull back line 220 from the coupling 212 is preconfigured, the deployment line 210 and the sleeve pull back line 220 can be pulled simultaneously by an operator. For example, tension can be applied to the sleeve pull back line 220 to cause sleeve retraction. Until the desired amount of sleeve retraction has occurred, pulling of the deployment line 210 can take up an offset in length between the deployment line 210 and the sleeve pull back line 220, and/or apply tension to the deployment line 210 to release the coupling 212 proximal to but not past a point of its engagement with the sleeve pull back line 220. Once the desired amount of sleeve retraction has occurred, release of the coupling 212 will have occurred at a point of its engagement with the sleeve pull back line 220.

Thus, by selecting an offset in length between the deployment line 210 and the sleeve pull back line 220 and/or selecting an axial position of a point of engagement of the coupling 212 with the sleeve pull back line 220, the relative timing of when disengagement of the sleeve pull back line 220 from the coupling 212 occurs, and thus how much the sleeve 200 is retracted by the sleeve pull back line 220, can be manipulated.

In this regard, releasing the coupling 212 (and deploying the underlying device) and sleeve retraction can begin at the same time, but sleeve retraction can cease shortly thereafter while the device deployment continues. In other embodiments, deploying the underlying device can begin prior to sleeve retraction. In still other embodiments, deploying the underlying device can begin after sleeve retraction.

In various embodiments, and turning now to FIG. 3, rather than being engaged to the coupling 312, the sleeve pull back line 320 can be engaged to an independent release line 330. In other words, the coupling 312 in various embodiments does not serve a dual function of closing the sleeve 300 and securing the sleeve pull back line 320. Instead, those functions are performed by separate lines, namely, the deployment line 310 and the release line 330. In this regard, by applying tension to the deployment line 310, the device can be completely deployed from the sleeve 300 before the sleeve 300 is retracted relative to or from the device. Such embodiments may find particular utility when a system comprises one or more additional sleeves to enable intermediate device deployment prior to full device deployment. When disengagement of the sleeve pull back line 320 from the release line 330 occurs (and thus how much the sleeve 300 is retracted by the sleeve pull back line 320) can either be determined manually or be preconfigured in the manners described above.

In various embodiments, a system comprises plurality of sleeve pull back lines, for example, 2, 3, 4, 5, or more, to apply tension substantially equally about the perimeter of a sleeve. For example, two sleeve pull back lines can mirror each other across a sagittal plane through the central axis of the sleeve 100.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

By way of example, while the deployment line has been illustrated as being outside the sleeve, and the sleeve pull back line as being inside the sleeve, either may be completely or partially outside the sleeve or inside the sleeve, and if inside the sleeve, either outside the endoluminal device or inside the endoluminal device.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An implantable system comprising:
    a sleeve having a distal end and a proximal end and configured to constrain an endoluminal device;
    a deployment line configured to form a coupling, the deployment line and coupling being configured to close the sleeve in constraining the endoluminal device; and
    a sleeve pull back line engaged to in a zig zag pattern near the proximal end of the sleeve, and engaged to the coupling through at least one hole in the sleeve;
    wherein applying tension to the sleeve pull back line retracts the sleeve whereby the zig zag pattern multiplies the tensile force applied to the sleeve; and
    wherein applying tension to the deployment line releases the coupling and deploys the endoluminal device.

2. The implantable system of claim 1, wherein at least one hole includes a plurality of holes, and the sleeve pull back line is engaged to the sleeve through the plurality of holes in the sleeve and wherein the sleeve includes an interior portion and an exterior portion, and the sleeve pullback line is located along the interior portion of the sleeve prior to engaging the sleeve and the coupling through the hole.

3. The implantable system of claim 1, wherein the sleeve pull back line is engaged to the coupling, and wherein applying tension to the deployment line releases the sleeve pull back line and breaks the tension therein.

4. The implantable system of claim 1, wherein the sleeve pull back line is engaged to a release line, and wherein applying tension to the release line releases the sleeve pull back line.

5. The implantable system of claim 3, wherein an amount by which the sleeve is retracted by the sleeve pull back line is proportional to an offset in length between the deployment line and the sleeve pull back line.

6. The implantable system of claim 3, wherein an amount by which the sleeve is retracted by the sleeve pull back line can be manipulated by selecting an axial position of a point of engagement of the coupling with the sleeve pull back line.

7. The implantable system of claim 1, wherein the sleeve pull back line is removeable.

8. The implantable system of claim 1, wherein the sleeve pull back line is fixedly engaged to the coupling.

9. The implantable system of claim 1, wherein the sleeve pull back line is moveably engaged to the sleeve through a hole.

10. The implantable system of claim 1, wherein the coupling is a chain stitch.

11. The implantable system of claim 1, wherein the endoluminal device is one of a stent, graft, filter, and valve.

12. The implantable system of claim 1, wherein the sleeve is comprised of expanded polytetrafluoroethylene.

13. An implantable system comprising:
    a sleeve comprising expanded polytetrafluoroethylene and constraining a stent or graft, the sleeve including an interior portion and an exterior portion;
    a deployment line configured to form a chain stitch along the exterior portion of the sleeve, the deployment line and coupling being configured to close the sleeve in constraining the stent of graft; and
    a sleeve pull back line engaged to the chain stitch and engaged to the sleeve and the coupling through a plurality of holes in the sleeve in a z-pattern, the sleeve pullback line being located along the interior portion of the sleeve prior to engaging the sleeve and the coupling through the plurality of holes;
    wherein applying tension to the sleeve pull back line retracts the sleeve whereby the z-pattern multiplies the tensile force applied to the sleeve;
    wherein applying tension to the deployment line releases the chain stitch and deploys the endoluminal device; and
    wherein applying tension to the deployment line releases the sleeve pull back line and breaks the tension therein after the chain stitch begins to be released and the endoluminal device begins to be deployed.

14. An implantable system comprising:
    a flexible sleeve for constraining an endoluminal device. the flexible sleeve including an interior portion and an exterior portion;
    a deployment line configured to form a coupling along the exterior portion of the sleeve, the deployment line and coupling being configured to close the sleeve in constraining the endoluminal device, wherein applying tension to the deployment line releases the coupling and deploys the endoluminal device; and
    a sleeve pull back line is coupled to a portion of the sleeve in a zig zag pattern and the coupling, such that the portion of the sleeve is retracted in response to selective tensioning of the sleeve pull back line whereby the zig zag pattern multiplies the tensile force applied to the sleeve, and the sleeve pullback line is located along the interior portion of the sleeve prior to engaging the coupling through the hole.

15. The implantable system of any of claim 14, wherein the sleeve pull back line is engaged to a release line, such that applying tension to the release line releases the sleeve pull back line.

16. The implantable system of any of claim 14, wherein the sleeve pull back line is operatively connected to the coupling, such that applying tension to the deployment line releases the sleeve pull back line.

17. The implantable system of claim 16, wherein an amount by which the sleeve is retracted by the sleeve pull back line can be manipulated by selecting an offset in length between the deployment line and the sleeve pull back line.

18. The implantable system of claim 16, wherein an amount by which the sleeve is retracted by the sleeve pull back line can be manipulated by selecting an axial position of a point of engagement of the coupling with the sleeve pull back line.

19. The implantable system of claim 14, wherein the sleeve pull back line is removably coupled to the sleeve.

20. The implantable system as set forth in claim 19, wherein the coupling is a chain stitch.

* * * * *